United States Patent [19]

Essen-Moller

[11] Patent Number: 5,820,556
[45] Date of Patent: Oct. 13, 1998

[54] METHOD AND APPARATUS FOR PRIMARILY AMBULATORY GASTROINTESTINAL REGISTRATION

[75] Inventor: Anders Essen-Moller, Stockholm, Sweden

[73] Assignee: Synectics Medical AB, Stockholm, Sweden

[21] Appl. No.: 676,276

[22] PCT Filed: Jan. 19, 1995

[86] PCT No.: PCT/SG95/00056

§ 371 Date: Sep. 17, 1996

§ 102(e) Date: Sep. 17, 1996

[87] PCT Pub. No.: WO95/20147

PCT Pub. Date: Jul. 27, 1995

[30] Foreign Application Priority Data

Jan. 19, 1994 [SE] Sweden .................................. 9400145

[51] Int. Cl.[6] ...................................................... A61B 5/00
[52] U.S. Cl. .......................................... 600/315; 600/343
[58] Field of Search ..................................... 128/632, 633, 128/634, 664, 665; 600/315, 343, 342, 341, 473, 476

[56] References Cited

U.S. PATENT DOCUMENTS

| | | | |
|---|---|---|---|
| 4,412,005 | 10/1983 | Wu | 436/97 |
| 4,632,119 | 12/1986 | Reichstein | 128/632 |
| 4,976,265 | 12/1990 | Falcial et al. | 128/634 |
| 5,438,985 | 8/1995 | Essen-Moller | 128/633 |

*Primary Examiner*—Jennifer Bahr
*Assistant Examiner*—Eric F. Winakur
*Attorney, Agent, or Firm*—Dowell & Dowell, P.C.

[57] ABSTRACT

A method for a preferably ambulatory measuring and registration of at least one parameter in relation to the bilirubin presence in a measuring region in the gastrointestinal tract of a patient to determine the bilirubin presence in the region. The method is characterized in that the bilirubin presence determination is made in relation to the pH-value of the fluids in the region. The invention relates also to a system for performing the method.

15 Claims, 1 Drawing Sheet

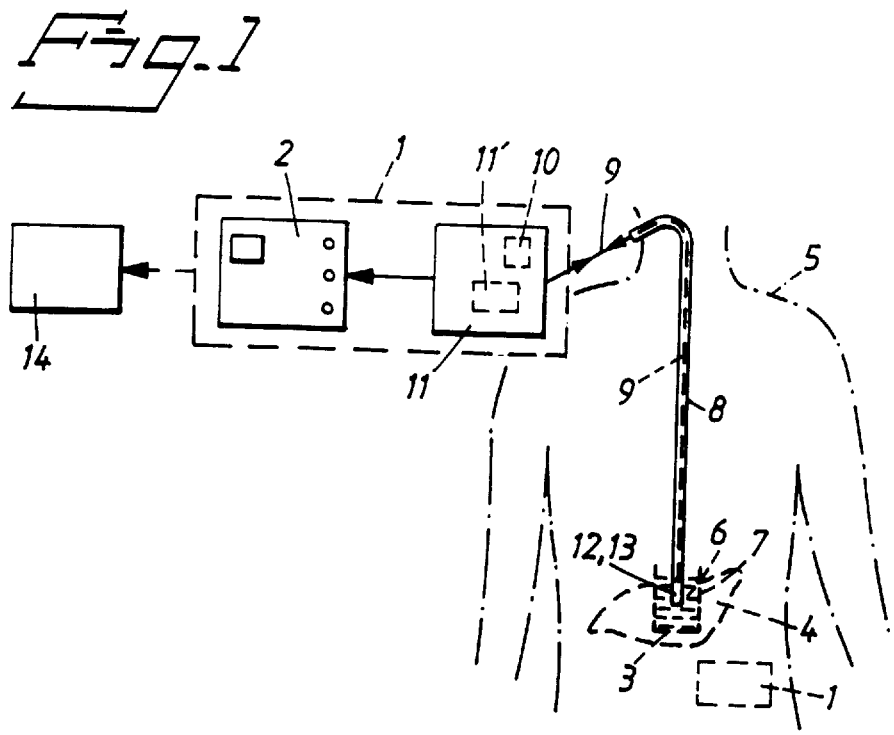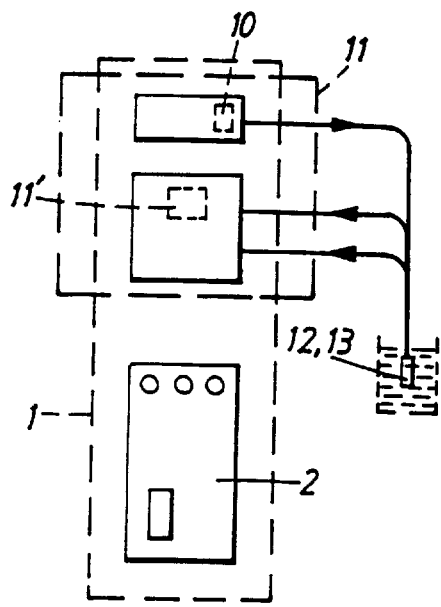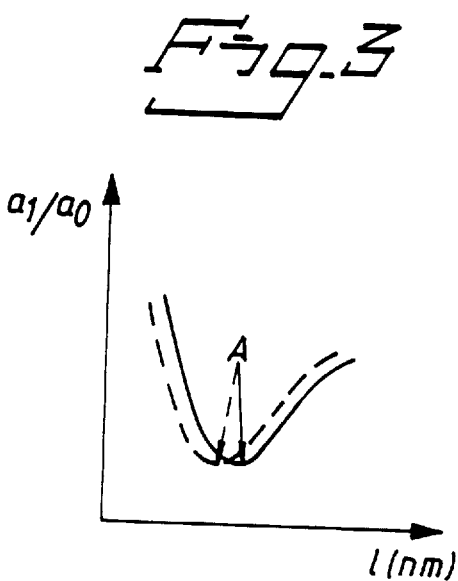

METHOD AND APPARATUS FOR PRIMARILY AMBULATORY GASTROINTESTINAL REGISTRATION

BACKGROUND OF THE INVENTION

1. Field of the Invention

The present invention relates to a method for a primarily ambulatory parameter registeration related to the presence of bilirubin in the gastrointestinal tract.

The invention also relates to a system for performing said method.

2. History of the Related Art

According to the state of art of essentially a fibreoptic means is inserted in the gastrointestinal tract and the light absorption at a wave length of about 460 nm is measured by means of spectrophotography, the wave length being indicated to correspond the maximum bilirubin absorption. Also, the light absorption is measured at a wavelength of 600 nm, being a reference length with a minimal bilirubin related absorption. This technology has been found to possibly provide absorption values for bilirubin containing more than a 10 precent error level or more. Errors in this magnitude are sufficient to make it impossible to distinguish patients with a normal bilirubin exposure in the measuring region of the gastrointestinal tract from patients with an abnormal exposure.

SUMMARY OF THE INVENTION

The present invention relates to a method and a system, with which reliable bilirubin related exposure measurements can be achieved.

BRIEF DESCRIPTION OF THE DRAWINGS

The invention is described here below more in detail with reference to an executed example and the attached drawings, wherein FIG. 1 illustrates schematically a first embodiment of a system according to the present invention for an ambulatory registration of i.a. the presence of bilirubin in the gastrointestinal tract, FIG. 2 shows schematically and in more detail a part of the system in FIG. 1, and FIG. 3 shows schematically the maximum absorption in relation to the pH-value.

In the preferred embodiment of the system shown in FIG. 1 and 2 with 1 is designated a registration unit for the ambulatory measurement and registration adapted to be carried by the patient together with the actual detecting means. Units of this kind are already known. According to a preferred embodiment the registration unit 1 thus comprises a Synectics MicroDigitrapper 2 being descbribed in the european patent No 0,356,603, by which means a plurality of measurement items, i.e. parameters such as a pH-value, can be registered.

The system includes means for the determination of at least one parameter depending on the presence of bilirubin in a measuring region 3 in the gastrointestinal tract 4 of a patient 5. The region is here shown schematically as a container 7 filled with a fluid 6.

For the determination of i.a. the light absorption in the measuring region a catheter 8 is provided adapted to run from the outside of the patient to the measuring region and including fibreoptical conducting means 9 adapted to conduct light by means of at least one light diode 10 or a similarly created light. The present light diodes 10 consist of measuring and control means 11, here illustrated separated from the unit 2, but which preferably are included in the registration unit as schematically illustrated in FIGS. 1 and 2. According to preferred embodiments means are provided in the form of light emitting diodes, fibreoptical conductors, sensor elements 12, etc., principally according to U.S. Pat. No. 4,976,265 to determine the amount of light absorption in the measuring region. The light is of a generally certain first wavelength $l_1$ corresponding to the maximum bilirubin light absorption in the measuring region and as a reference to determine the amount of light absorption in the measuring region, this light being of a generally certain second wavelength $l_0$ corresponding to the minimum bilirubin light absorption, schematically shown spectrophotographical means 11' preferably being provided in the measuring and control means to analyze the light from the measuring region.

Furthermore, there are, according to the invention, provided means, e.g. comprising an antimony crystal sensor 13 for measuring the pH-value in the measuring region, the pH-value related measuring values being adapted to be carried to the measuring and control means 11, said means according to an embodiment being adapted to control the absorption determination in relation to the pH-value.

According to a first embodiment the first wavelength is however provided to be, by means of the measuring and control means 11, chosen on the basis of an actual pH-value, as the wavelength $l_1$ corresponding to the the maximum absorption A, FIG. 3, is changed in relation to the pH-value. For a pH-value over 3.5, for example, $l_1$ is chosen to have a value of e.g. 460 nm and for a pH-value below 3.5 $l_1$ is chosen to have another, diverging from said first value. This can be achieved by using alternative light emitting diodes 10 or similar. It is also possible that at least $l_1$ acccording to this embodiment essentially varies continuously with the pH-value by means of a convenient light emitting diode. Combinations of gradual and continuous changes are also possible of the $l_1$ with the pH-value. The changes in the maximum absorption A is shown schematically in FIG. 3, the relation between the absorption $a_1$ and $a_0$ for $l_1$ and $l_0$, respectively, shown as a function of $l_1$ and both curves representing different pH-values, with $l_0$ e.g. being 600 nm.

According to a second embodiment, the measuring and control means are preferably adapted to form the basis for a correction, preferably basing on previous measurements, of at least the first wavelength $l_1$. An example of such a correction is given here below:

$$b_{cor} = b_{read} \times K$$

where $b_{cor}$=corrected absorption $b_{read}$=measured absorption, and

K=a corection factor, related to the pH-value

According to this example, K=1 for a pH-value over 3.5 and K=1.2 for a pH-value below 3.5. The quoted formula is an example and can naturally be improved to achieve a finer correction. Said correction is not necessarily performed by means of the measuring and control unit, but can also be proformed later on in the registrating unit 2 or during an analysis of the measuring values by means of an external unit, see FIG. 1, to which the information from the registration unit 1 is adapted to be transmitted.

During the absorption measuring also the light intensity can be varied in a compensating and finely adjusting way.

The performance and the function of the system according to the invention has been generally presented here above. According to the all comprising function, the determination of the bilirubin presence is thus related to the pH-value, and preferably essentially all pH-value and all actual parameters are used. Especially during a light absorption measuring the measurings are adapted to the pH-value by means of the wavelength or the measuring values are corrected biased on the pH-value by means of a preferably empirically defined correction relation.

As seen from the above, the invention provides the possibility to most essentially and even decisively increase the reliability of the measured presence of bilirubin in the gastrointestinal tract.

The invention has been described in connection to an executed example. Of course, further embodiments and minor changes and can therefore be imagined without departing from the scope of the invention.

The invention primarily relates to bilirubin, but can even be used for several other substances being present in the gastrointestinal tract. The description and the claims are therefore to be interpreted so that in any case bilirubin possibly can be substituted by any other substance.

According to an embodiment being preferred in many cases said first wavelength is set to about 450 nm at a pH-value of 3.5 and to about 400 nm at a pH-value<3.5. It is then preferred that also the other wavelength is about 565 nm.

Thus, the invention is supposed not to be restricted to the embodiments stated above, but can be varied wthin the scope of the attached claims.

I claim:

1. A method for determining the presence of bilirubin in a measuring region of the gastrointestinal tract of a patient comprising the steps of:
    a) determining a pH value of fluid within the measuring region;
    b) introducing light at a first wavelength value related to the maximum light absorption of bilirubin into the measuring region and detecting a light absorption value at the first wavelength value of the fluid within the measuring region and introducing light at a second wavelength value related to the minimum light absorption by bilirubin into the measuring region and detecting the light absorption value at the second wavelength value of the fluid within the measuring region;
    c) calculating the ratio of the light absorption value at the first wavelength value to the light absorption value at the second wavelength value and adjusting the ratio dependent upon the pH value determined for the fluid in the measuring region to thereby obtain a determination for the presence of bilirubin in the measuring region.

2. The method of claim 1 including the step of selecting said first wavelength value based upon the pH value determined for the fluid in the measuring region.

3. The method of claim 2 wherein said first wavelength has a value of approximately 460 nm at pH values greater than approximately 3.5 and a value of less than 460 nm at pH values of less than 3.5.

4. The method of claim 3 including the step of continuously varying said first wavelength dependent upon the pH value determined.

5. The method of claim 1 including the steps of introducing a fiber optic means into the measuring region for introducing light at the first and second wavelength values to the measuring region and wherein the detecting of the light absorption values is analyzed utilizing a process of spectrophotography.

6. The method of claim 5 wherein the determination of pH value includes a step of introducing an antimony crystal sensor into the measuring region.

7. The method of claim 1 wherein said determining of the pH level and the detecting of the light absorption values of the fluids within the measuring region at the first and second wavelengths is carried out while the patient is ambulatory.

8. The method of claim 1 wherein the adjusting of the ratio of the light absorption value at the first wavelength to the light absorption value at the second wavelength is corrected by a multiplication factor based upon the pH value determined for the fluid in the measuring region.

9. The method of claim 8 wherein the multiplication factor is selected equal to one for pH values over 3.5 and greater than one for pH values below 3.5.

10. A system for determining the presence of bilirubin in fluid of a measuring region of the gastrointestinal tract of a patient, the system comprising:
    a) sensor means for sensing the pH value of the fluid within the measuring region;
    b) a light emitting source for emitting light at first and second wavelengths, a fiber optic conductor extending from said light source to the measuring region;
    c) detector means for detecting light transmitted through said fiber optic conductor and through the fluid in the measuring region and conveying detected information to a measuring and control unit receiving input from the sensor means and including means for determining the light absorption of the fluid within said measuring region at said first and second wavelengths to thereby determine the presence of bilirubin in the measuring region dependent upon the input from the sensor means.

11. The system of claim 10 in which said measuring and control unit includes a spectrophotography means for analyzing input from said detector means.

12. The system of claim 11 in which said light emitting source includes at least one diode and means for varying the wavelengths emitted from said at least one diode.

13. The system of claim 12 in which said measuring and control unit includes means for varying said first wavelength from said at least one diode dependent upon a pH value determined from said pH sensor.

14. The system of claim 13 in which said pH sensor includes an antimony crystal sensor.

15. The system of claim 10 wherein the system includes a registration unit in which said measuring and control unit and said light emitting source are housed, said registration unit being ambulatory with a patient.

* * * * *

UNITED STATES PATENT OFFICE
CERTIFICATE OF CORRECTION

PATENT NO. : 5,820,556
DATED : October 13, 1998
INVENTOR(S) : Anders Essen-Moller It is certified that error appears in the above—identified patent and that said Letters Patent is hereby corrected as shown below:

On the title page, item [86]:
Please delete "PCT/SG95/00056 and insert --PCT/SE95/00056--

Signed and Sealed this

Twenty-sixth Day of January, 1999

Attest:

Attesting Officer

*Acting Commissioner of Patents and Trademarks*